US00PP22573P2

(12) United States Plant Patent
Brown

(10) Patent No.: US PP22,573 P2
(45) Date of Patent: Mar. 13, 2012

(54) ***MANDEVILLA* PLANT NAMED 'ALEGNUFLOR702'**

(50) Latin Name: *Mandevilla hybrida*
Varietal Denomination: Alegnuflor702

(75) Inventor: Graham Noel Brown, Pennant Hills (AU)

(73) Assignees: Floraquest Pty. Ltd., Pennant Hills, NSW (AU); Protected Plant Promotions Australia Pty. Ltd., Macquarie Fields, NSW (AU)

( * ) Notice: Subject to any disclaimer, the term of this patent is extended or adjusted under 35 U.S.C. 154(b) by 0 days.

(21) Appl. No.: 12/931,177

(22) Filed: Jan. 26, 2011

(51) Int. Cl.
*A01H 5/00* (2006.01)

(52) U.S. Cl. ..... Plt./232

(58) Field of Classification Search ..... Plt./232
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Alegnuflor702', characterized by its compact, upright and mounding plant habit; strong stems; early and freely flowering habit; and light red purple-colored flowers.

1 Drawing Sheet

Botanical designation: *Mandevilla hybrida.*
Cultivar denomination: 'ALEGNUFLOR702'.

CROSS-REFERENCED TO CLOSELY-RELATED APPLICATIONS

Title: *Mandevilla* Plant Named 'ALEGNUFLOR704'
Applicant: Graham Noel Brown
Filed: U.S. Plant patent application Ser. No. 12/931,163
Title: *Mandevilla* Plant Named 'ALEGNUFLOR709'
Applicant: Graham Noel Brown
Filed: U.S. Plant patent application Ser. No. 12/931,164
Title: *Mandevilla* Plant Named 'ALEGNUFLOR711'
Applicant: Graham Noel Brown
Filed: U.S. Plant patent application Ser. No. 12/931,168
Title: *Mandevilla* Plant Named 'ALEGNUFLOR714'
Applicant: Graham Noel Brown
Filed: U.S. Plant patent application Ser. No. 12/931,176

BACKGROUND OF THE INVENTION

The present invention relates to a new and distinct cultivar of *Mandevilla* plant, botanically known as *Mandevilla hybrida* and hereinafter referred to by the name 'Alegnuflor702'.

The new *Mandevilla* plant is a product of a planned breeding program conducted by the Inventor in Pennant Hills, New South Wales, Australia. The objective of the breeding program is to create new shrub-type *Mandevilla* plants with strong stems and numerous attractive flowers.

The new *Mandevilla* plant originated from a cross-pollination made by the Inventor in Pennant Hills, New South Wales, Australia in December, 2003, of a proprietary selection of *Mandevilla hybrida* identified as code number X02.5, not patented, as the female, or seed parent with *Mandevilla hybrida* 'Sunmandecrim', disclosed in U.S. Plant Pat. No. 15,539, as the male, or pollen, parent. The new *Mandevilla* plant was discovered and selected by the Inventor as a single flowering plant from within the progeny of the stated cross-pollination in a controlled greenhouse environment in Macquarie Fields, New South Wales, Australia in January, 2008.

Asexual reproduction of the new *Mandevilla* plant by cuttings in Macquarie Fields, New South Wales, Australia, since January, 2008, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in cultural practices and environment such as temperature and light intensity without, however, any variance in genotype.

The following traits have been repeatedly observed and are determined to be the unique characteristics of 'Alegnuflor702'. These characteristics in combination distinguish 'Alegnuflor702' as a new and distinct *Mandevilla* plant:

1. Compact, upright and mounding plant habit.
2. Strong stems.
3. Early and freely flowering habit.
4. Light red purple-colored flowers.

Plants of the new *Mandevilla* can be compared to plants of the female parent selection. Plants of the new *Mandevilla* differ from plants of the female parent selection in the following characteristics:

1. Plants of the new *Mandevilla* are more compact than and not as vining as plants of the female parent selection.
2. Plants of the new *Mandevilla* flower earlier than plants of the female parent selection.
3. Plants of the new *Mandevilla* have smaller flowers than plants of the female parent selection.

Plants of the new *Mandevilla* can be compared to plants of the male parent, 'Sunmandecrim'. Plants of the new *Mandevilla* differ from plants of 'Sunmandecrim' in the following characteristics:

1. Plants of the new *Mandevilla* are more compact than and not as vining as plants of 'Sunmandecrim'.
2. Plants of the new *Mandevilla* and 'Sunmandecrim' differ in flower color as plants of 'Sunmandecrim' have crimson red-colored flowers.

Plants of the new *Mandevilla* can be compared to plants of *Mandevilla hybrida* 'Alegnuflor704', disclosed in U.S. Plant patent application Ser. No. 12/931,163; *Mandevilla hybrida* 'Alegnuflor709', disclosed in U.S. Plant patent application Ser. No. 12/931,164; *Mandevilla hybrida* 'Alegnuflor711', disclosed in U.S. Plant patent application Ser. No. 12/931,168; and *Mandevilla hybrida* 'Alegnuflor714', disclosed in U.S. Plant patent application Ser. No. 12/931,176. Plants of the new *Mandevilla* differ primarily from plants of 'Alegnuflor704', 'Alegnuflor709', 'Alegnuflor711', 'Alegnuflor714' in flower bud and flower color.

Plants of the new *Mandevilla* can be compared to plants of *Mandevilla hybrida* 'Ginger', disclosed in U.S. Plant Pat. No. 20,776. Plants of the new *Mandevilla* differ primarily from plants of 'Ginger' in the following characteristics:

1. Plants of the new *Mandevilla* are more compact than plants of 'Ginger'.
2. Plants of the new *Mandevilla* have smaller leaves and flowers than plants of 'Ginger'.

Plants of the new *Mandevilla* can also be compared to plants of *Mandevilla hybrida* 'Sunparapibra', disclosed in U.S. Plant Pat. No. 19,649. Plants of the new *Mandevilla* differ primarily from plants of 'Sunparapibra' in the following characteristics:

1. Plants of the new *Mandevilla* are more compact than plants of 'Sunparapibra'.
2. Plants of the new *Mandevilla* have smaller flowers than plants of 'Sunparapibra'.
3. Flowers of plants of the new *Mandevilla* are darker in color than flowers of plants of 'Sunparapibra'.

BRIEF DESCRIPTION OF THE PHOTOGRAPH

The accompanying colored photograph illustrates the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant. The photograph comprises a side perspective view of a typical flowering plant of 'Alegnuflor702' grown in a container.

DETAILED BOTANICAL DESCRIPTION

The aforementioned photograph and following observations, measurements and values describe plants grown in 12.5-cm containers during the spring and summer in a polyethylene-covered greenhouse in Cobbitty, New South Wales, Australia and under commercial production cultural practices. During the production of the plants, day temperatures ranged from 18° C. to 38° C. and night temperatures ranged from 5° C. to 21° C. Plants were 14 weeks old when the photograph and description were taken. In the following description, color references are made to The Royal Horticultural Society Colour Chart, 2001 Edition, except where general terms of ordinary dictionary significance are used.

Botanical classification: *Mandevilla hybrida* 'Alegnuflor702'.

Parentage:

*Female, or seed, parent.*—Proprietary selection of *Mandevilla hybrida* identified as code number X02.5, not patented.

*Male, or pollen, parent.*—*Mandevilla hybrida* 'Sunmandecrim', disclosed in U.S. Plant Pat. No. 15,539.

Propagation:

*Type.*—By cuttings.

*Time to produce a rooted young plant.*—About one month.

*Root description.*—Fleshy, thick; white in color.

*Rooting habit.*—Moderate branching; medium density.

Plant description:

*Plant and growth habit.*—Compact, upright and mounding plant habit, slightly vining; moderately vigorous growth habit.

*Plant height.*—About 30 cm.

*Plant diameter.*—About 33 cm.

*Lateral branch description.*—Branching habit: Moderate branching habit with about four primary lateral branches per plant; primary laterals with secondary laterals; pinching enhances lateral branch development. Length: About 25 cm. Diameter: About 5 mm. Internode length: About 4.5 cm. Strength: Strong. Texture: Smooth, glabrous. Color: Close to 144A.

Foliage description:

*Arrangement.*—Opposite, simple.

*Length.*—About 7 cm.

*Width.*—About 4.5 cm.

*Shape.*—Broadly elliptical.

*Apex.*—Acuminate.

*Base.*—Obtuse.

*Margin.*—Entire.

*Texture, upper and lower surfaces.*—Smooth, glabrous; leathery.

*Venation pattern.*—Pinnate, arcuate.

*Color.*—Developing leaves, upper and lower surfaces: Close to 146A. Fully expanded leaves, upper surface: Close to 139A; venation, close to 146A. Fully expanded leaves, lower surface: Close to 147A; venation, close to 145A.

*Petioles.*—Length: About 1.5 cm. Diameter: About 3 mm. Texture, upper and lower surfaces: Smooth, glabrous. Color, upper surface: Close to 146C. Color, lower surface: Close to 146A.

Flower description:

*Flower type and habit.*—Salverform flowers arranged in loose terminal and axillary clusters; flowers face upright or outwardly; freely flowering habit, about five flowers and flower buds per cluster.

*Natural flowering season.*—Plants initiate flower buds about six weeks after planting; plants flower continuously year-round in the greenhouse and outdoors from spring to early winter in New South Wales, Australia.

*Flower longevity on the plant.*—About three to four days; flowers not persistent.

*Fragrance.*—None detected.

*Flowers.*—Appearance: Funnelform with five-parted fused corolla; flowers roughly star-shaped. Diameter: About 8 cm. Depth (length): About 7 cm. Throat diameter: About 1.8 cm. Tube length: About 5 cm. Tube diameter, at the base: About 4 mm.

*Flower buds.*—Height: About 7 cm. Diameter: About 1.4 cm. Shape: Elongated oblong. Color: Close to 63A.

*Corolla.*—Arrangement/appearance: Single whorl of five petals, imbricate and fused into a flared trumpet. Petal lobe length: About 4 cm. Petal lobe width: About 2.5 cm. Petal lobe shape: Roughly elliptical. Petal apex: Acute. Petal margin: Entire. Petal texture, upper and lower surfaces: Smooth, glabrous; velvety. Throat texture: Smooth, glabrous; velvety. Tube texture: Smooth, glabrous. Color: Petal lobe, when opening, upper surface: Close to 58A. Petal lobe, when opening, lower surface: Close to 59B. Petal lobe, fully opened, upper surface: Close to 58C; color becoming closer to 59A with development. Petal lobe, fully opened, lower surface: Close to 58A. Throat: Close to 21A. Tube: Close to 145A.

*Sepals.*—Arrangement/appearance: Five per flower fused in a single whorl. Length: About 7 mm. Width: About 2 mm. Shape: Lanceolate. Apex: Acute. Margin: Entire. Texture, upper and lower surfaces: Smooth, glabrous. Color, inner surface: Close to 145C. Color, outer surface: Close to 145B.

*Peduncles.*—Length: About 5 cm. Diameter: About 2 mm. Texture: Smooth, glabrous. Strength: Strong, flexible. Aspect: About 45° from the stem axis. Color: Close to 144A.

*Pedicels.*—Length: About 2 cm. Diameter: About 2 mm. Texture: Smooth, glabrous. Strength: Strong, flexible. Aspect: About 20° to 35° from the peduncle axis. Color: Close to 144A.

*Reproductive organs.*—Stamens: Quantity per flower: Typically five. Filament length: About 1.5 mm. Filament color: Close to 158C. Anther shape: Narrowly oblong. Anther size: About 8 mm by 2 mm. Anther color: Close to 158A. Pollen amount: Scarce. Pollen color: Close to 155A. Pistils: Quantity per flower: Typically one. Pistil length: About 2.7 cm. Stigma shape: Rounded; five-lobed. Stigma color: Close to 145A. Style length: About 2.2 cm. Style color: Close to 145C. Ovary color: Close to 146C.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 5° C. to about 38° C.

It is claimed:

1. A new and distinct *Mandevilla* plant named 'Alegnuflor702' as illustrated and described.

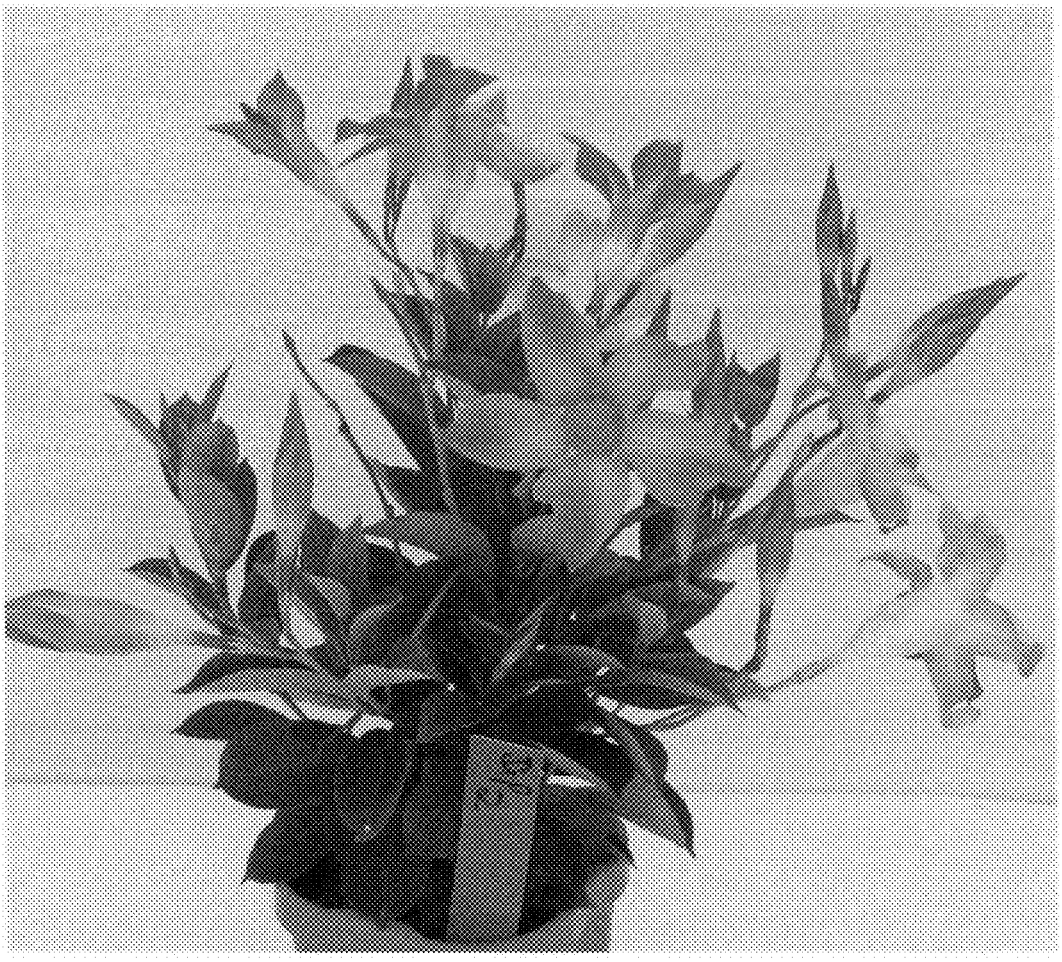

* * * * *